United States Patent [19]

Guigan

[11] Patent Number: 4,463,097
[45] Date of Patent: Jul. 31, 1984

[54] METHOD AND DEVICE FOR BRINGING A LIQUID SAMPLE SUCCESSIVELY INTO CONTACT WITH A NUMBER OF REAGENTS

[76] Inventor: Jean Guigan, 9, rue Jean Mermoz, 75008 Paris, France

[21] Appl. No.: 384,703

[22] Filed: Jun. 3, 1982

[30] Foreign Application Priority Data

Jun. 5, 1981 [FR] France .............................. 81 11158

[51] Int. Cl.³ ...................... G01N 35/00; G01N 21/01
[52] U.S. Cl. .................................... 436/45; 356/427; 422/64; 422/72; 422/102; 436/43; 436/180
[58] Field of Search ............... 356/244, 246, 426, 427; 366/237, 239; 422/63, 64, 72, 102, 104; 436/43, 45, 180; 494/16, 17, 28, 33, 34

[56] References Cited

U.S. PATENT DOCUMENTS 3,547,547  12/1970  Anderson ........................ 356/246 X
4,083,638   4/1978  Sandrock et al. ............... 422/102 X
4,135,883   1/1979  McNeil et al. .................... 422/55 X
4,390,499   6/1983  Curtis et al. ...................... 422/64 X Primary Examiner—Michael S. Marcus
Assistant Examiner—Michael S. Gzybowski
Attorney, Agent, or Firm—Sughrue, Mion, Zinn, Macpeak, and Seas

[57] ABSTRACT

In a method and device for bringing a liquid sample successively into contact with a number of reagents, contact with the reagents is effected in a series of cells. These cells communicate with one another and are carried by a rotor, transfer of the liquid sample from one cell to another being effected by rotating the rotor. The direction of rotation of the rotor is reversed after each transfer operation. The number of cells constituting the series is at least equal to the number of reagents. The reagents are placed in the cells beforehand.

4 Claims, 2 Drawing Figures

METHOD AND DEVICE FOR BRINGING A LIQUID SAMPLE SUCCESSIVELY INTO CONTACT WITH A NUMBER OF REAGENTS

BACKGROUND OF THE INVENTION

1. Field of the Invention

The present invention concerns a method and a device for bringing a liquid sample successively into contact with a number of reagents, in order to analyze the sample.

2. Description of the Prior Art

At the present time to carry out such an analysis it is possible either to transfer the sample from container to container, each container holding the appropriate reagent, or to introduce the various reagents successively into the same container.

Whichever process is used, carrying out the analysis operations requires an apparatus which is more or less complex and which is installed at a fixed point, so ruling out the possibility of carrying out analyses at the place where the liquid sample is taken.

It is also known, for example from French Pat. No. 2 441 401, to use centrifugal force to transfer a sample to be analyzed and a reagent into a compartment in which they mix and then into an analysis vessel. This process is not adapted to the case of a number of reagents, especially when a reaction time must be allowed to elapse between the addition of the reagents.

An objective of the present invention is to overcome the aforementioned disadvantages.

SUMMARY OF THE INVENTION

The invention consists in a method for bringing a liquid sample successively into contact with a number of reagents by means of a series of intercommunicating cells carried by a rotor, the number of cells in the series being at least equal to the number of reagents, which are placed in the cells beforehand, transfer of the liquid sample from one cell to another being achieved by rotating the rotor and the direction of rotation of the rotor being reversed after each transfer of the liquid sample.

In other words, when the rotor turns in one direction the sample can only pass from a first cell to a second cell, transfer from the second cell to a third being prevented and being possible only when the direction of rotation of the rotor is reversed.

In a preferred embodiment of the invention, a metered quantity of the liquid sample is introduced into the first cell in the series and the last cell in the series may constitute a measuring cell for the purposes of analyzing the sample.

The invention further consists in a device for implementing the method as defined above.

This device includes a rotor comprising a container having a vertical axis and presenting a number of series of cells, and means whereby the cells of each series communicate with one another disposed so that on rotation of the rotor in a first direction the sample may be transferred from a first cell to a second cell and may not be transferred to the cell preceeding the first cell or following the second cell, means being provided to reverse the direction of rotation of the rotor after each transfer from one cell to another.

In this way it is a very simple matter using a single device to apply whatever time interval may be required in bringing the liquid sample into contact with two successive reagents.

In a preferred embodiment of the invention, the cells in the same series are disposed in two adjacent and substantially radial rows, a wall delimiting the two rows carrying means whereby the cells communicate with one another.

The aforementioned communication means may advantageously comprise orifices in the upper part of said wall, each cell having a curved profile surface leading from the bottom of the cell to the orifice whereby the liquid sample is transferred from one cell to the next.

Other characteristics of the invention will appear from the following description, when considered in connection with the accompanying drawings.

DESCRIPTION OF THE PREFERRED EMBODIMENT

Figure 1:
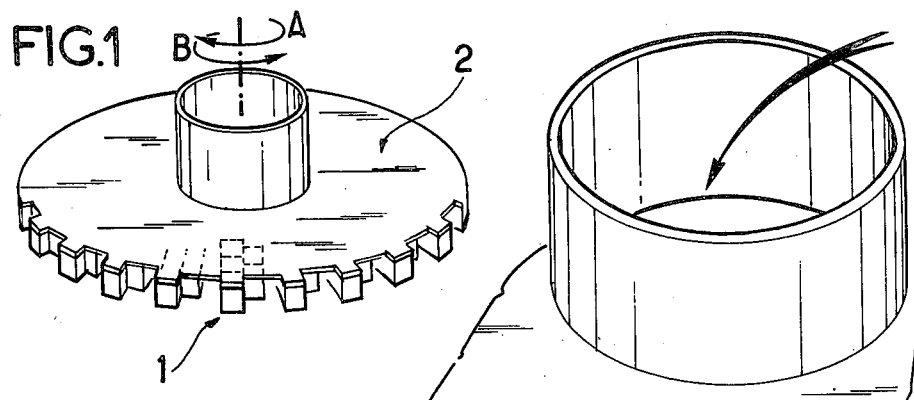
FIG. 1 is a schematic view in perspective of an analysis device in accordance with the invention.

The analysis device 1 in accordance with the invention includes a rotor comprising a container 2 having a vertical axis and presenting a number of series of receptor cells. The rotor is able to rotate in a first direction (A) and in the opposite direction (B). Each series of cells comprises a plurality of cells disposed substantially along a radius of the rotor.

A series comprises two adjacent and substantially radial rows of cells.

The first row comprises cells 3, 5 and 7, the second cells 4 and 6.

A common wall 8 delimits the two rows. The means whereby a cell communicates with the next in the same series consist in orifices 9, 10, 11 and 12 in said wall 8, in the upper part thereof.

The cells preferably have a curved profile surface 13 leading from the bottom of the cell to the orifice whereby the liquid sample is transferred to the next cell.

Figure 2:
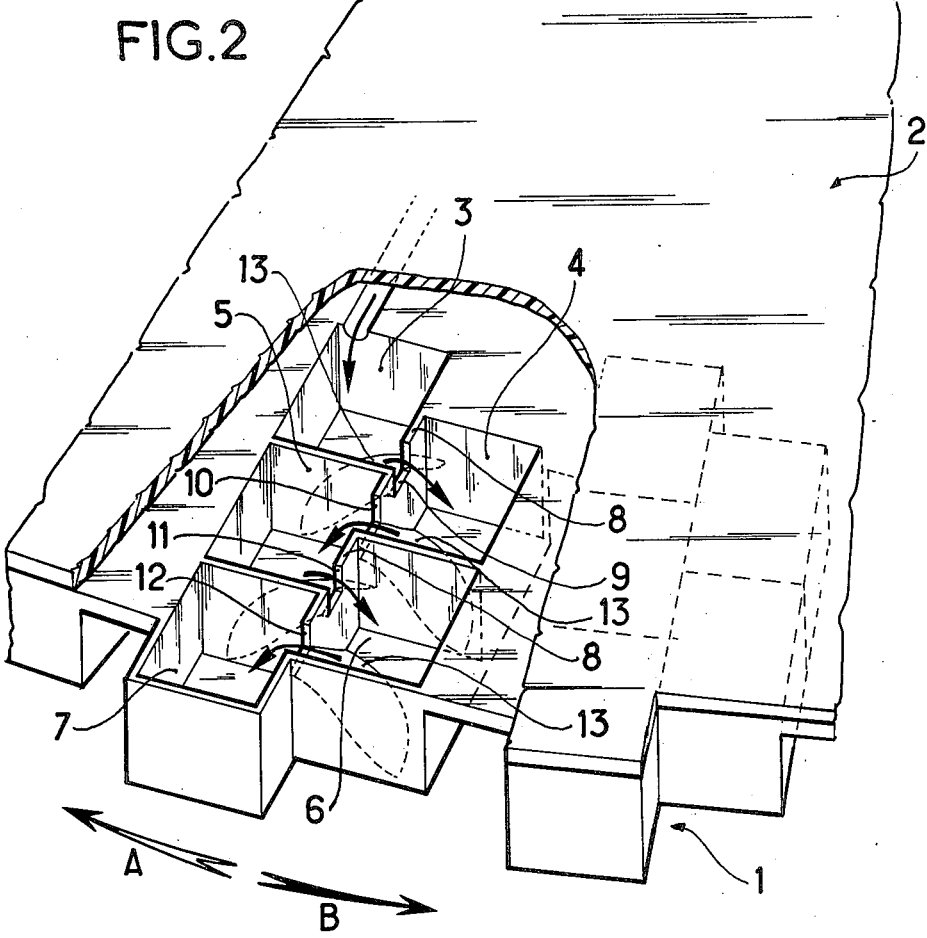
FIG. 2 is a partially cut away view of the device shown in FIG. 1, to a larger scale.

As can be clearly seen in FIG. 2, it is not necessary to provide a curved profile surface for admitting the sample into the cell.

OPERATION

The device operates in the following manner:

A metered quantity of the liquid sample is introduced into the cell 3 in the series closest the center of the rotor.

Also, reagents are placed beforehand in cells 3 to 7, in freeze-dried form, for example. It will be understood that if the analysis involves bringing the liquid sample into contact with a number of reagents less than a number of cells in the series, certain of the cells will not hold any reagent.

With the liquid sample to be analyzed in cell 3, after a time sufficient for the reaction with the reagent in this cell to be completed the rotor is rotated in the direction defined by arrow B. By virtue of centrifugal force, the liquid is moved towards the corner of the cell comprising the curved profile and via orifice 9 enters cell 4 where it comes into contact with a second reagent.

It will be readily apparent that by virtue of centrifugal force when the rotor rotates in direction B the liquid which enters cell 4 via orifice 9 cannot escape from it, either via orifice 9 or via the orifice 10 leading to cell 5.

The rotor may be stopped or maintained in rotation in direction A for the time needed for the reaction to occur in cell 4. The rotor is then rotated in direction A, whereupon the liquid sample is transferred via orifice 10 into cell 5 where it comes into contact with another reagent.

As outlet orifice 10 of cell 4 is further outwards in the radial direction than inlet orifice 9, and by virtue of curved profile 13, the liquid sample cannot escape from cell 4 other than via orifice 10 on rotation in direction A.

After the reaction in cell 5, the rotor is rotated in direction B and the liquid sample is then transferred via orifice 11 into cell 6 where it comes into contact with another reagent. It is not possible for it to return to cell 4 via orifice 10, for the reasons already explained.

After the reaction in cell 6, the rotor is rotated in direction A and the liquid sample is then transferred via orifice 12 into cell 7 where it may be brought into contact with another reagent if required.

Cell 7, the last cell in the series, may constitute a measuring cell for carrying out photometric or colorimetric measurements, for example, using appropriate apparatus (not shown). A reading may be taken substantially perpendicular to the radius of the rotor or perpendicular to the median plane of the container.

The rotor may be molded and may be made of a synthetic resin.

The metered quantity of the liquid sample may be introduced into cell 3 by any appropriate means.

However, the device and the process described in U.S. patent application Ser. No. 336,130 may advantageously be used.

The aforementioned application discloses apparatus for dispensing a predetermined dose of a sample liquid into a receptor cell on a rotor, so as to analyze it, said rotor comprising a container having a vertical axis and in which is formed an annular basin having radial partitions delimiting compartments serving as receptacles for said liquid sample and a number of receptor cells regularly distributed around the annular basin, means for conveying the liquid being provided between each compartment of the basin and each receptor cell.

The aforementioned device is characterized in that the aforementioned liquid conveying means comprise a measurement chamber having an inlet orifice in communication with said compartment and an outlet orifice, preferably of a capillary nature, said two orifices delimiting in the measurement chamber a defined volume, means being provided at the outlet from said measurement chamber for directing the liquid issuing therefrom either to an overflow chamber when the rotor is rotating in a first direction or to the receptor cell when the rotor is rotating in the opposite direction.

The means provided at the outlet from the measurement chamber comprise a flow channel extending substantially radially from the measurement chamber to the receptor cell, said channel being provided with a branch leading to the overflow chamber from a point immediately downstream from the outlet orifice and on the same side of said outflow channel as the measurement chamber.

The aforementioned device operates as follows:

In a first stage a quantity of the liquid sample of greater volume than can be contained in the measurement chamber is introduced into a compartment in the annular basin. In a second stage, the rotor is rotated in the first direction which results in the displacement of all the liquid contained in said compartment into the measurement chamber through the inlet orifice and the filling of the measurement chamber, the excess liquid leaving said measurement chamber through the outlet orifice to the overflow chamber. Finally, in a third stage, the rotor is rotated in the opposite direction as a result of which all the liquid contained in the measurement chamber is expelled therefrom into the receptor cell.

The aforementioned device for delivering a metered quantity of the liquid sample may be situated on the rotor shown in the drawings, on the upstream side of the first cell 3 of the series of cells in which contact with the reagents is effected, cell 3 then constituting the receptor cell of the aforementioned device, the process for dispensing a predetermined dose of a liquid sample into said cell 3 preceeding the bringing of the sample successively into contact with the reagents in cells 3 to 7.

Means (not shown) are provided for evacuating air during centrifuging operations.

The device in accordance with the invention allows simultaneous analysis of several samples of liquid which are distributed in various series of cells such as 3 to 7 which are spaced out angularly around the periphery of the device.

It is claimed:

1. A method for bringing a liquid sample successively into contact with a number of reagents by means of a series of intercommunicating cells carried by a rotor, the number of cells in said series being at least three and at least equal to the number of reagents, which are placed in said cells beforehand, said method comprising the steps of:
    transferring said liquid sample from a first cell to an adjacent cell by rotating said rotor and
    transferring said liquid in a sequential manner through subsequent cells by reversing the direction of rotation of said rotor after each transfer of said liquid sample from one cell to the adjacent cell.

2. A method according to claim 1, wherein the cells in said series are disposed in two adjacent and substantially radial rows, a wall delimits said two rows and said transfer is effected by passing said liquid sample through said wall from a cell in one row to a cell in the other row; whereby said cells communicate with one another.

3. A method according to claim 1, wherein a metered quantity of said liquid sample is introduced into the first, radially inboard cell in said series and the last, radially outboard cell in said series constitutes a measuring cell for the purposes of analyzing said sample.

4. A method according to claim 1, wherein said reagents are placed in said cells in freeze-dried form.

* * * * *